United States Patent
Beelman et al.

(10) Patent No.: US 8,337,921 B2
(45) Date of Patent: Dec. 25, 2012

(54) METHODS AND COMPOSITIONS FOR IMPROVING THE NUTRITIONAL CONTENT OF MUSHROOMS AND FUNGI

(75) Inventors: Robert B. Beelman, University Park, PA (US); Michael Kalaras, Wernersville, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/563,065

(22) Filed: Jul. 31, 2012

(65) Prior Publication Data
US 2012/0294994 A1    Nov. 22, 2012

Related U.S. Application Data

(62) Division of application No. 12/386,810, filed on Apr. 23, 2009, now abandoned.

(60) Provisional application No. 61/047,268, filed on Apr. 23, 2008.

(51) Int. Cl.
*A23L 1/303*  (2006.01)
(52) U.S. Cl. .......................................... 426/248; 426/73
(58) Field of Classification Search .................. 426/248, 426/73
See application file for complete search history.

(56) References Cited

U.S. PATENT DOCUMENTS

| | | | |
|---|---|---|---|
| 5,123,203 A | 6/1992 | Hiromoto | |
| 5,427,592 A | 6/1995 | Romaine et al. | |
| 7,258,882 B2 | 8/2007 | Hankinson et al. | |
| 2005/0287255 A1 | 12/2005 | Notermans | |
| 2007/0204507 A1 | 9/2007 | Miller et al. | |
| 2009/0274806 A1 | 11/2009 | Schroeder | |
| 2009/0304880 A1 | 12/2009 | Kidder et al. | |
| 2010/0223843 A1 | 9/2010 | Williams | |
| 2011/0091579 A1 | 4/2011 | Hausman | |

FOREIGN PATENT DOCUMENTS

| JP | 57-189660 A | 11/1982 |
|---|---|---|
| JP | 04-183369 A | 6/1992 |

OTHER PUBLICATIONS

Vitamin D Formation from Post-Harvest Pulsed Light Treatment of Mushrooms, Xenon Corporation, Jul. 30, 2008, Roger Williams, pp. 1-4.*
Computer translation of KR 10-0637833, Oct. 2006.*
Lee, J., et al., "The Effect of UV-B Irradiation and Hot-Air Drying on the Vitamin D2 Contents of Shiitake Mushroom (*Lentinus edodoes*)", Korean J. Soc. Food Cookery Sci., 18(2):173-178 (2002).

(Continued)

*Primary Examiner* — Drew E Becker
(74) *Attorney, Agent, or Firm* — McKee Voorhees & Sease, P.L.C.

(57) ABSTRACT

An improved filamentous fungi is disclosed that has an enhanced nutritional profile by utilizing pulsed ultraviolet irradiation. According to the invention, the vitamin D component of mushrooms and other filamentous fungi may be drastically increased with no deleterious affects on appearance with the use of pulsed UV radiation. Mushrooms so treated had up to 1800% DV in one serving of fresh mushrooms.

20 Claims, 9 Drawing Sheets

OTHER PUBLICATIONS

Jasinghe, V.J., et al., "Distribution of ergosterol in different tissue of mushrooms and its effect on the conversion of ergosterol to vitamin D2 by UV irradiation", Food Chemistry 92:541-546 (2005).

Jasinghe, V.J., et al., "Ultraviolet irradiation: The generator of Vitamin D2 in edible mushrooms", Food Chemistry 95:638-643 (2006).

Teichmann, A., et al., "Sterol and vitamin D2 concentrations in cultivated and wild grown mushrooms: Effects of UV irradiation", J. LWT Science Direct: 40:815-822 (2007).

The Penn State Research Foundation, PCT/US2009/041516, filed Apr. 23, 2009, International Search Report mailed Feb. 4, 2010.

JP 57-189660A, Fukuhara, English translation of Abstract, Nov. 1982.

JP 04-183369A, Kawazoe, English translation of Abstract, Jun. 1992.

Chikthimmah, Naveen et al., "Microbiology of Fruits and Vegetables", CRC Press 2005, pp. 135-158.

* cited by examiner

METHODS AND COMPOSITIONS FOR IMPROVING THE NUTRITIONAL CONTENT OF MUSHROOMS AND FUNGI

CROSS-REFERENCE TO RELATED APPLICATIONS

This is a Divisional application of U.S. Ser. No. 12/386,810 filed Apr. 23, 2009, which application claims priority under 35 U.S.C. §119 of a provisional application Ser. No. 61/047,268 filed Apr. 23, 2008, each of which are hereby incorporated by reference in their entirety.

GRANT REFERENCE

This invention was made with government support under Hatch Act Project No. PEN04092, awarded by the USDA and No. 58-0790-6-051, awarded by the USDA/ARS. The Government has certain rights in the invention.

FIELD OF THE INVENTION

This invention relates to a nutritional product for use in animal feed, foods and beverages and more particularly to a mushroom or fungi having an increased vitamin content.

BACKGROUND OF THE INVENTION

Mushrooms are valuable health food—low in calories, high in vegetable proteins, chitin, iron, zinc, fiber, essential amino acids, vitamins & minerals. Mushrooms also have a long history of use in traditional Chinese medicine. Their legendary effects on promoting good health and vitality and increasing a body's adaptive abilities have been supported by Western medicine as well. They are an excellent source of selenium, riboflavin, pantothenic acid, copper, niacin, potassium and phosphorous. Selenium is needed for the proper function of the antioxidant system, which works to reduce the levels of damaging free radicals in the body. Selenium is a necessary cofactor of one of the body's most important internally produced antioxidants, glutathione peroxidase, and also works with Vitamin E in numerous vital antioxidant systems throughout the body.

Mushrooms are also the only vegetable or fruit which contains Vitamin D, naturally. All other natural food sources of Vitamin D are of animal, poultry or seafood origin. Also, some foods, such as milk, orange juice and cereals may be fortified with Vitamin D, up to 100 IU.

Vitamin D is a fat-soluble vitamin that is naturally present in very few foods, added to others, and available as a dietary supplement. It is also produced endogenously when ultraviolet rays from sunlight strike the skin and trigger Vitamin D synthesis. So one must either ingest Vitamin D or sit in the sun and soak up UV rays, so that it may be synthesized endogenously. The risks of sun exposure have gained much attention lately, and the association of sun exposure with Precancerous (actinic keratosis) and cancerous (basal cell carcinoma, squamous cell carcinoma and melanoma) skin lesions—caused by loss of the skin's immune function, fine and coarse wrinkling of the skin, freckles, discoloration of the skin, and Elastosis—the destruction of the elastic tissue causing lines and wrinkles is well documented. Thus as people become more sensitive to the dangers of UV exposure, other dietary sources of Vitamin D become increasingly important for maintaining health.

Vitamin D is essential for promoting calcium absorption in the gut and maintaining adequate serum calcium and phosphate concentrations to enable normal mineralization of bone and prevent hypocalcemic tetany. It is also needed for bone growth and bone remodeling by osteoblasts and osteoclasts. Without sufficient Vitamin D, bones can become thin, brittle, or misshapen. Vitamin D sufficiency prevents rickets in children and osteomalacia in adults. Together with calcium, Vitamin D also helps protect older adults from osteoporosis.

Vitamin D has other roles in human health, including modulation of neuromuscular and immune function and reduction of inflammation. Many genes encoding proteins that regulate cell proliferation, differentiation, and apoptosis are modulated in part by Vitamin D. Many laboratory-cultured human cells have Vitamin D receptors and some convert 25(OH)D to 1.25(OH)$_2$D. It remains to be determined whether cells with Vitamin D receptors in the intact human carry out this conversion.

It is an object of the present invention to provide a food product for use in foods and beverages which is high in nutritional values, particularly Vitamin D.

It is another object of the invention to provide methods for enhancing the Vitamin D content of mushrooms.

It is yet another object of the invention to provide such nutritionally enhanced mushrooms and filamentous fungi without any deleterious affects on the mushrooms appearance.

These and other objects of the present invention will become apparent from the description of the invention which follows.

SUMMARY OF THE INVENTION

This invention creates an improved food product with an enhanced nutritional profile by utilizing ultraviolet irradiation. The product is obtained by a method comprising the steps of obtaining a mushroom or other fungi the content of Vitamin D or its analogs or derivatives, of which is desired to be increased. The mushroom or fungi is subjected to pulsed UV irradiation. Applicants have discovered the dosage and timing of radiation (pulsing) to provide the highest benefit of increased Vitamin D content, without any negative effects on mushroom appearance, shelf life, or nutrients. These benefits were shown to be stable, even after more than one week in storage. The pulsed UV minimizes the damaging effects of ultra-violet radiation both from a mushroom quality as well as commercial preparation and workplace safety standpoint. Utilizing the irradiation in discrete pulses was shown to enhance the Vitamin D content on the order of eight to ten times the content of Vitamin D over non-irradiated mushroom or fungi. The effect was also demonstrated to not adversely affect other nutritionally desirable components of mushrooms and was shown to be effective at increasing Vitamin D when applied to mushroom tissues, components, or even to spent mushroom substrate. In yet another embodiment, the Vitamin D enriched mushroom substrate could be used in animal feed or as a nutritional source of Vitamin D. Mushrooms are usually produced by first preparing a substrate, such as corn, rice, millet or rye, prepared by soaking the grain in water and sterilizing the substrate before inoculation with mushroom spores or mushroom mycelia. Mycelia are the filamentous hyphae of a mushroom that collect water and nutrients to enable mushrooms to grow. The inoculated substrate is then held to promote colonization of the mycelia, at which point the mycelia-laced grains become "spawn". This is usually done in individual spawn bags. The substrate provides the nutrients necessary for mycelium growth. The mycelium-impregnated substrate then develops under controlled temperature and moisture conditions, until the hyphae of the mycelium have colonized the substrate. The mycelium enriched product usually is harvested after about four to eight weeks from the beginning of the process, with the contents of the spawn bag possibly processed into dry powdered product. According to the invention, this spent substrate may also be enriched in Vitamin D upon application of pulsed UV irradiation.

As used herein the term "mushroom" or "filamentous fungi" shall be interpreted to include all tissues, cells, organs of the same, including but not limited to mycelium, spores, gills, fruiting body, stipe, pileus, lamellae, basidiospores, basidia, and the like.

DETAILED DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
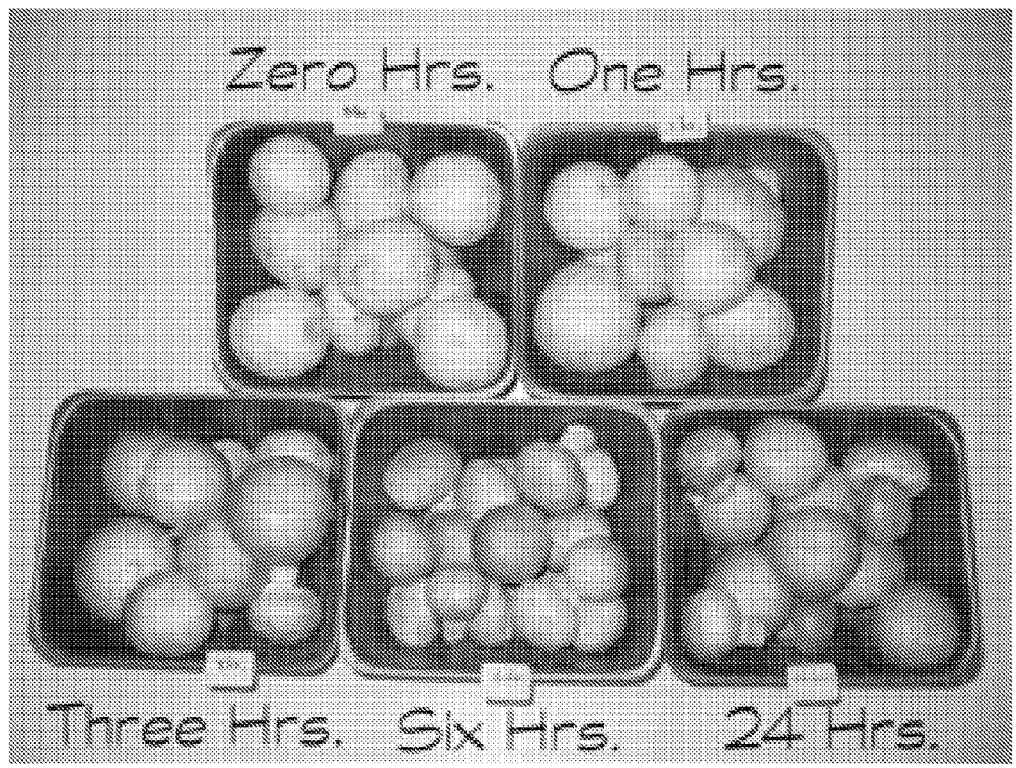
FIG. 1 is a photograph of UV treated mushrooms by the methods of Feeney et al.

Previous research (Feeney, 2006) determined that exposing mushrooms to constant ultraviolet light can produce Vitamin $D_2$ by converting the naturally-occurring ergosterol to Vitamin $D_2$. However, there were concerns about compliance with nutrition labeling regulations throughout retail distribution, deleterious affects on appearance, and tissue browning, See FIG. 1. Another significant disadvantage was the increased length of exposure time required by conventional sources of UV light, which were impractical in a packinghouse environment. Thus constant UV radiation at sufficient time and strength caused deleterious affects on the appearance of mushrooms and at best, achieved an increase of 100% of the % DV/per serving of Vitamin D but with a host of regulatory, and commercial processing concerns.

Chikthimmah and Beelman (2006) recently tested pulsed UV-light treatments at very high levels for long period of time (30 seconds or more) to reduce bacterial populations in fresh mushrooms. In this paper, they speculated that Vitamin $D_2$ content in mushrooms could be rapidly increased using pulsed UV-light. The conclusion was, however that such exposure caused discoloration and deleterious affects on the appearance of mushrooms, particularly white mushrooms. Such browning of mushrooms would make them commercially undesirable. Bacterial populations are responsible for the browning and degradation of mushrooms, which has a dramatic and negative affect on their appeal to customers.

Figure 2:
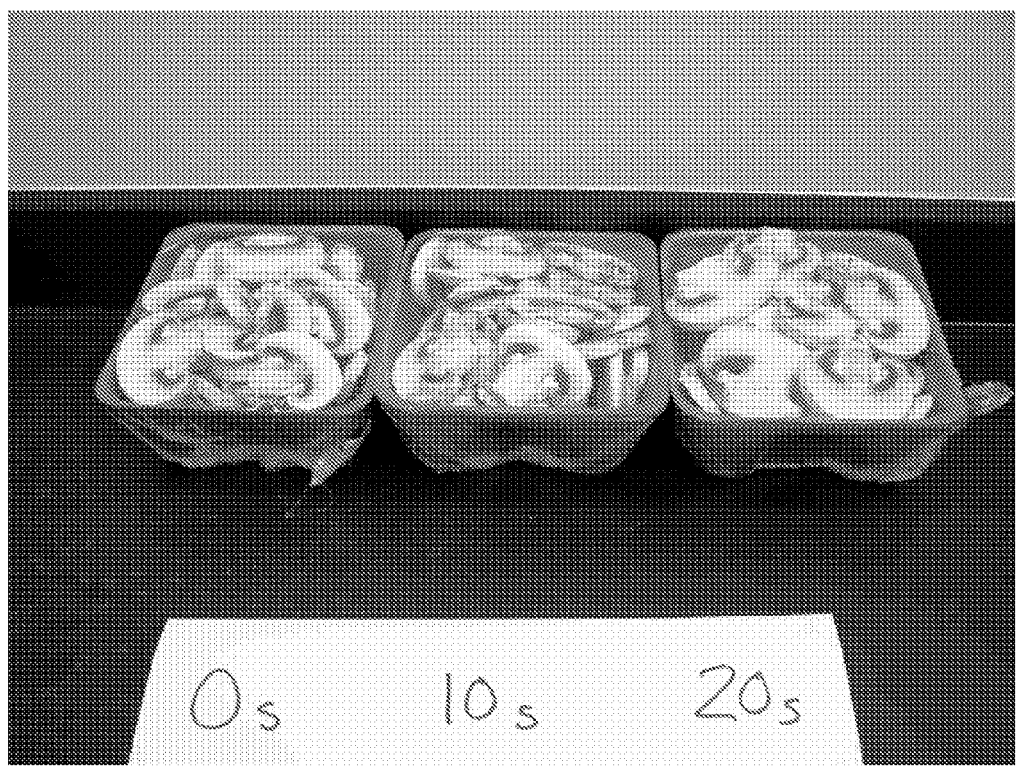
FIG. 2 is a photograph of pulsed UV treated mushrooms according to the invention.

According to the invention, applicant herein demonstrates that pulsed UV light at lower ranges and for very brief periods was shown to have dramatic increases in the Vitamin D levels present in such mushrooms, with increases by as much as 800 times the % DV (percent daily value) of Vitamin D content, per serving with no deleterious affects on the morphology or appearance of the mushroom. See FIG. 2. This dramatic increase in Vitamin D content in light of earlier studies which had demonstrated less Vitamin D conversion after much longer periods of UV exposure is quite surprising.

Pulsed UV-light treatments to increase Vitamin $D_2$ content in mushrooms were conducted with a laboratory scale, pulsed light sterilization system (SteriPulse®-XL 3000, Xenon Corporation, Woburn, Mass.) that is present in the Department of Agricultural Biological Engineering at Penn State. While applicants postulate that it is the UVB component of the Xenon pulsed light system that is responsible for the affects of the invention, it should be noted that the system uses pulsed light which includes the entire spectrum of light and may also include other components that contribute to the affects demonstrated herein and which are intended to be within the scope of the invention.

According to the invention, pulses of UV radiation of approximately 1-10 $J/cm^2$ per pulse, preferably 3-8 $J/cm^2$ and most preferably 5-6 $J/cm^2$ is used. Voltages may also vary based upon safety concerns but should generally be in the range or 1 to 10 or even up to 100 or 10,000 volts as safety mandates. The pulses should generally be in a range of 1-50 pulses per second more preferably 1-30 pulses per second and most preferably 1-10 pulses per second for a range of treatment post harvest of 0 to 60 seconds.

Any type of mushroom, mushroom part, component, fungi or even used substrate for cultivating mushrooms, with ergosterol present may be used. This includes all filamentous fungi where ergosterol has been shown to be present and includes the use of tissues such as the mycelia, spores or vegetative cells. This includes, but is not limited to, for example, *Coprinus, Agrocybe, Hypholoma, Hypizygus, Pholiota, Pleurotus, Stropharia, Gardonerma, Grifola, Trametes, Hercicium, Tramella, Psilocybe, Agaricus, Phytophtora, Achlya, Flammulina, Melanoleuca, Agrocybe, Grifola, Moschella, Mastigomycotina, Auricularia, Gymnopilus, Mycena, Boletus, Gyromitra, Pholiota, Calvatia, Kuegneromyces, Phylacteria, Cantharellus, Lactarius, Pleurotus, Clitocybe, Lentinula* (*Lentinus*), *Stropharia, Coprinus, Lepiota, Tuber, Tremella, Drosophia, Leucocoprinus, Tricholoma, Dryphila, Marasmius*, and *Volvariella*.

Non-limiting examples of other fungal genera, including fermentable fungi, include: *Alternaria, Endothia, Neurospora, Aspergillus, Fusarium, Penicillium, Blakeslea, Monascus, Rhizopus, Cephalosporium, Mucor*, and *Trichoderma*.

In yet another embodiment, the spent mushroom substrate upon which mushrooms are cultivated, was enriched in Vitamin D using pulsed UV light according to the invention. Such spent substrate could then be used as nutritional feed supplements and the like for animals.

The inventors used 5.61 J/cm$^2$ per pulse on the strobe surface for an input voltage of 3800V and with 3 pulses per second. Sliced mushrooms (*Agaricus bisporus*, white strain) were placed in the pulsed UV-light sterilization chamber and treated with pulsed light for up to a 20-second treatment at a distance of 17 cm from the UV lamp or 11.2 cm from the window. Control samples did not undergo any pulsed UV treatment. Treated mushrooms were freeze-dried and then sent to a selected commercial laboratory for Vitamin $D_2$ analysis. In this study, a pulsed UV system was also evaluated for effects on the appearance of fresh mushroom slices during a shelf life study.

Figure 3:
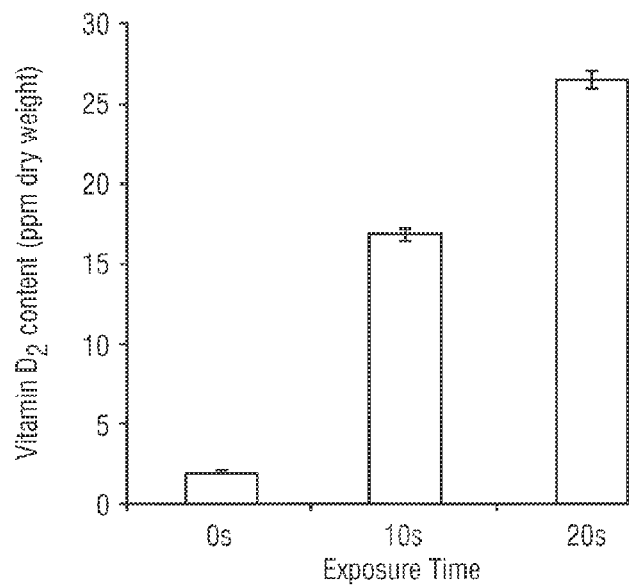
FIG. 3 is a graph depicting the Vitamin $D_2$ content of fresh sliced mushrooms after exposure to pulsed UV-light at 0, 10 and 20 seconds (C-type lamp).
Figure 4:
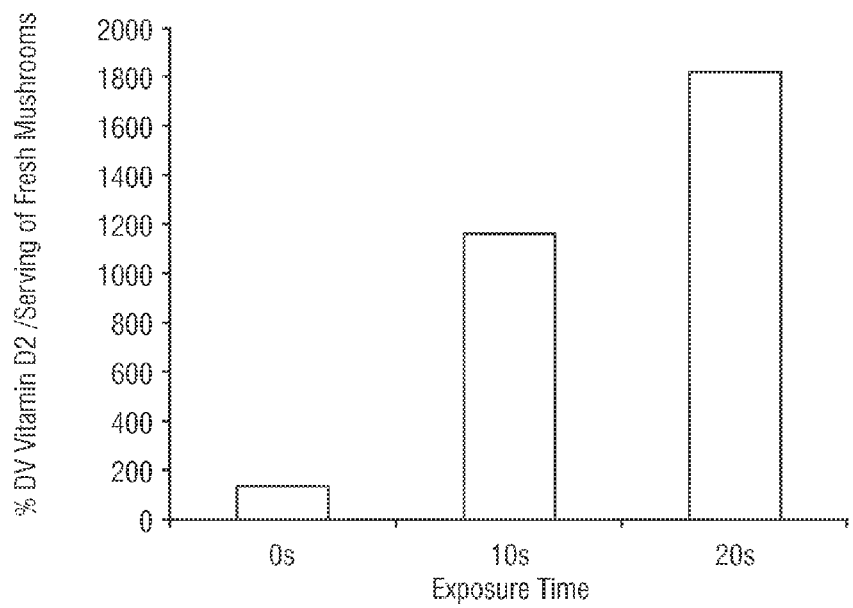
FIG. 4 is a graph depicting the Percent DV of Vitamin $D_2$ in one serving of fresh sliced mushrooms after exposure to pulsed UV-light at 0, 10 and 20 seconds (C-type lamp).
Figure 5:
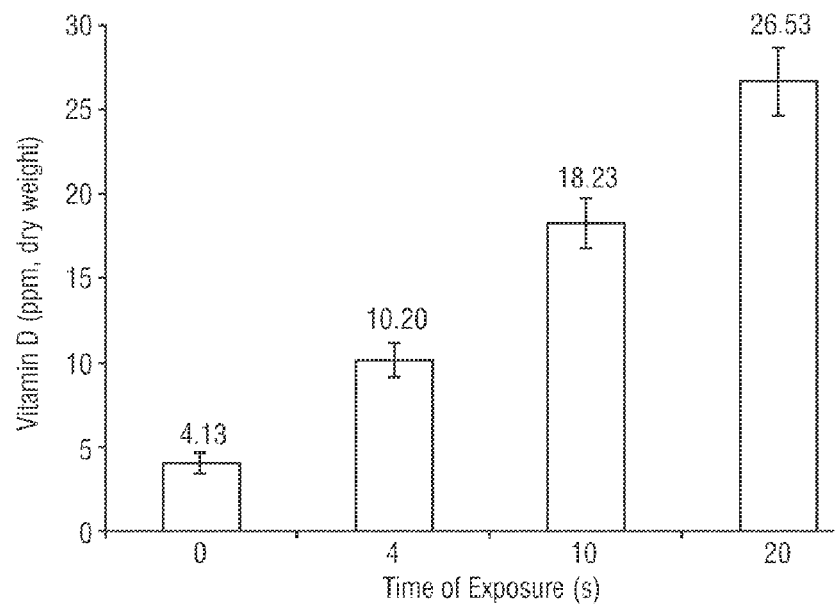
FIG. 5 is a graph depicting the Vitamin $D_2$ content of fresh sliced mushrooms after exposure to pulsed UV light at 0, 4, 10 and 20 seconds (C-type lamp).
Figure 6:
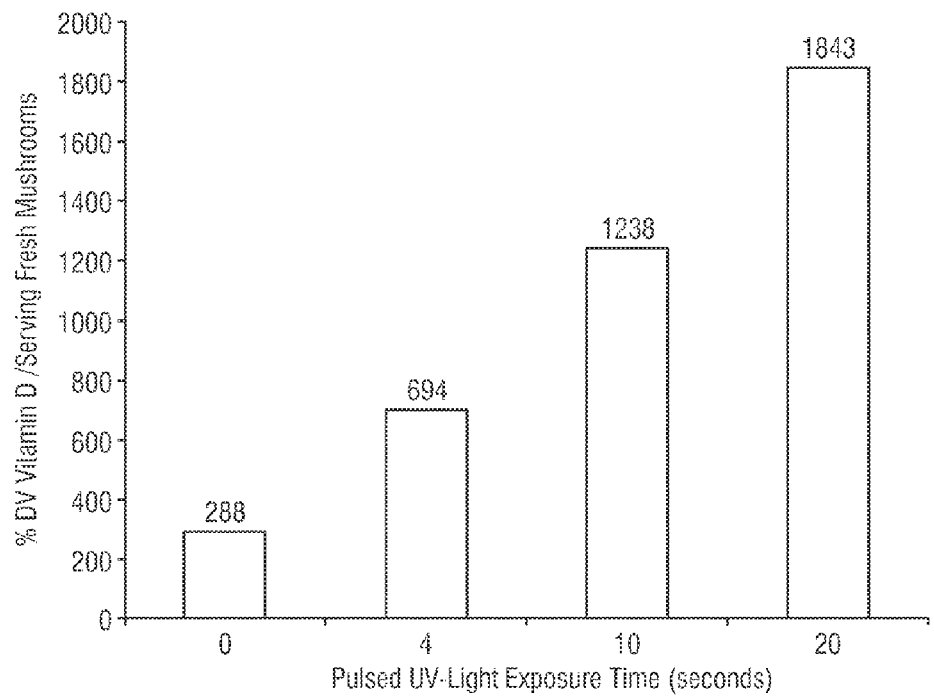
FIG. 6 is a graph depicting the Percent DV of Vitamin $D_2$ in one serving of fresh sliced mushrooms after exposure to pulsed UV-light (C-type lamp).

Results of the experiments demonstrated that pulsed UV-light was very effective in rapidly converting ergosterol to Vitamin $D_2$. Control mushrooms contained 2 ppm d.w. Vitamin $D_2$, while 10 and 20 seconds of exposure to pulsed UV-light resulted in 17 and 26 ppm Vitamin $D_2$, respectively (FIG. 3). This increase was equivalent to over 1800% DV Vitamin D in one serving of fresh mushrooms after a 20 second exposure to pulsed UV (FIG. 4). The mushrooms treated for 20 seconds also showed no noticeable difference in appearance initially as well as after 10 days of storage at 3° C. compared to the untreated control.

These results compared favorably to the previous pilot study (Feeney, 2006) where mushrooms were exposed to 5 minutes of conventional UV-light exposure. In that study, the mushrooms contained 14 ppm Vitamin $D_2$, but they were also significantly discolored. Hence, the pulsed UV method shows considerable promise as a rapid means to enhance Vitamin $D_2$ levels in fresh mushrooms, theoretically reducing required exposure times from minutes to seconds. Pulsed UV-light exposure did not result in any negative effects on mushroom quality.

Another experiment revealed that pulsed UV-light could rapidly convert ergosterol present in dried oyster mushroom powder to Vitamin $D_2$ (Table 1). These findings indicate that this technology could be used to enrich other mushroom products with Vitamin $D_2$.

TABLE 1

Vitamin $D_2$ generation in dried oyster mushroom powder exposed to pulsed UV-light (C-type lamp).

| Time of Exposure(s) | Vitamin $D_2$ (PPM) |
|---|---|
| 0 | 8.5 |
| 8 | 15.18 |
| 16 | 24.24 |

The present invention relates to methods for obtaining a nutritionally enhanced food product using pulsed UV radiation to increase Vitamin D and/or its derivatives in filamentous fungi. The solid substrate can be any part of the mushroom or mold, including the mycelia, spores etc, so long as ergosterol is present in at least part of the tissue or cells.

In the present invention, the filamentous fungi product is subjected to pulsed UV irradiation after harvest, being irradiated with UV light for a time sufficient to enhance the Vitamin D content thereof. By utilizing UV irradiation, the food product has a substantially increased level of Vitamin D. Preferably, the food product is irradiated with UV radiation, specifically Ultraviolet-B (UV-B), a section of the UV spectrum, with wavelengths between about 280 and 320 nm, or Ultraviolet-C (UV-C), with wavelengths between about 200 and 280 nm. In a more preferred embodiment the UV radiation is pulsed. It is believed that the additional Vitamin D is obtained through the conversion of ergosterol due to the UV irradiation. The time may be the same or increased when the irradiation occurs during the growing process, or post harvest though the UV irradiation can occur during both periods.

EXAMPLE 1

Fresh mushrooms were obtained from Modern Mushroom Farm (Avondale, Pa.) and the Penn State MTDF. All mushrooms were protected from extraneous light exposure throughout the experiments.

A Steripulse®-XL 3000 (Xenon Corporation, Wilmington, Mass.) was used for Pulsed UV light exposure. A B-type lamp was used. The system generated 505 Joules per pulse. At 3.2 cm from the window or 9 cm from the lamp, the broadband energy was 0.873 J/cm$^2$ per pulse. The system generates 3 pulses per second. All previous experiments were conducted using a Xenon C-type lamp.

Brown and white button mushrooms were sliced to expose gill tissue. They were randomly placed in 150 g lots into polystyrene containers. Oyster and Shiitake mushrooms were divided into 150 g lots and were arranged in the system so that there was a single layer of mushrooms. All samples were placed in the Pulsed UV system at a distance of 3.2 cm from the quartz window.

Brown and white button mushrooms were exposed for 0, 1, 2, 3, and 4 pulses. All treatments were repeated three times. Oyster and Shiitake mushrooms were exposed for 0, 1, 2, and 3 pulses. All treatments were repeated twice.

Mushroom powders from air-dried *Agaricus bisporus* with and without selenium enrichment grown at the Penn State MTDF using the methods of Werner and Beelman (2002), were treated in 5 g lots in uncovered Petri plates at a distance of 3.2 cm from the quartz window. King Oyster mushrooms (obtained from Golden Gourmet Mushrooms, San Marcos, Calif.) were air-dried and treated at the same distance. The powders were treated at 0, 4, 8, and 16 pulses.

Spent mushroom substrates (Maitake and King Oyster) obtained from Golden Gourmet Mushrooms were treated either before or after air drying. Dry samples were treated in 5 g lots and wet samples were treated in 20 g lots. The Maitake substrate was treated at 0, 4, and 8 pulses. King Oyster substrates were treated at 0, 8 and 16 pulses.

Commercially dried King Oyster mycelial biomass grown on sterile organic oats at Golden Gourmet Mushrooms (Mushroom Matrix) were treated at 0, 4, 8, and 16 pulses before and after being ground into powder form.

The King Oyster mushroom powder was also evaluated for ergothioneine content. Ergothioneine content was determined by the method of Dubost et al (2006). Ergothioneine levels are reported as mg/g dry weight.

Mushroom samples were freeze-dried directly following treatment and ground into powder. All other samples were air-dried and ground into powders. The powders were sent to Medallion Labs (Minneapolis, Minn.) for Vitamin $D_2$ analysis.

Vitamin $D_2$ values of fresh mushrooms are presented based on the % DV (Adequate Intake of 400 IU) in a serving (84 g) of fresh mushrooms. Vitamin $D_2$ values for powders and substrates are presented as IU/100 g dry weight.

Results and Discussion

After exposure to increasing amounts of pulsed UV light there was an increase in Vitamin $D_2$ content of every mushroom product tested. With each additional pulse the mushrooms were exposed to increasing amounts of irradiation and thus more energy was available for Vitamin $D_2$ synthesis from ergosterol.

Figure 7:
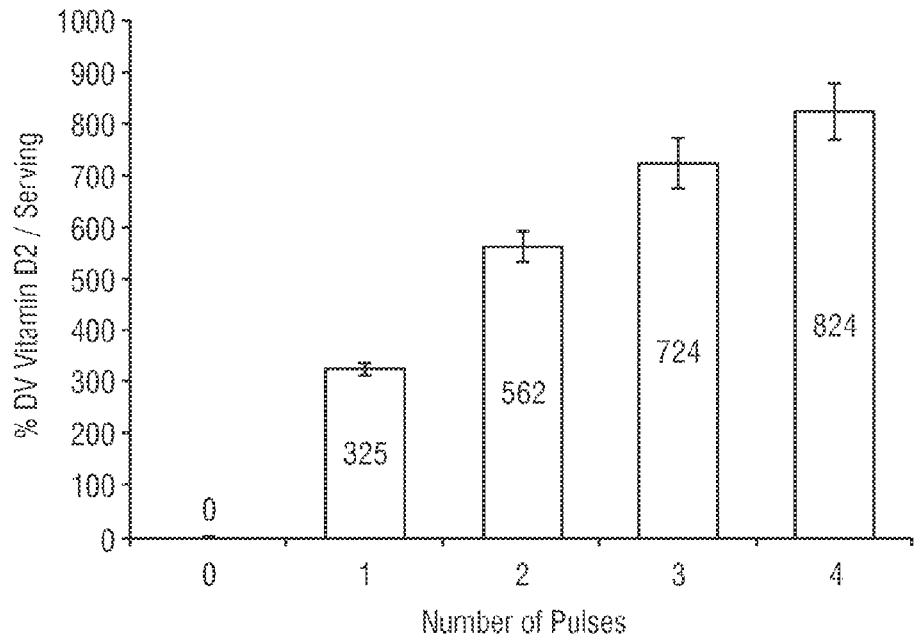
FIG. 7 is a graph showing the Percent DV Vitamin $D_2$ in one serving (84 g) of white button mushrooms (*Agaricus bisporus*) after pulsed UV light exposure (B-type lamp). Error bars represent standard deviation of the three replications.

Fresh sliced white button mushrooms showed an increase from an initial Vitamin $D_2$ level of 0% DV/serving to 325% DV/serving after just one pulse (FIG. 7). After 4 pulses the level of Vitamin $D_2$ increased to 824% DV/serving.

Figure 8:
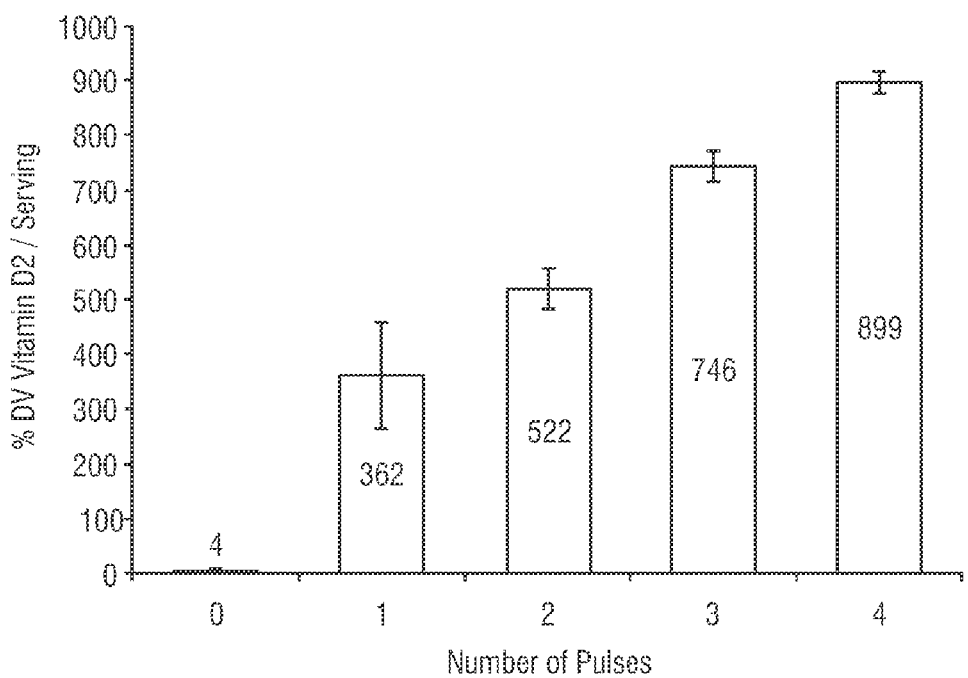
FIG. 8 is a graph depicting the percent DV Vitamin $D_2$ in one serving (84 g) of brown button mushrooms (*Agaricus bisporus*) after pulsed UV light exposure (B-type lamp). Error bars represent standard deviation of the three replications.

Fresh sliced brown button mushrooms (FIG. 8) Vitamin $D_2$ went from an initial level of 4% DV/serving at 0 pulses to 362% DV/serving after one pulse. The level increased to 899% DV/serving after 4 pulses.

Figure 9:
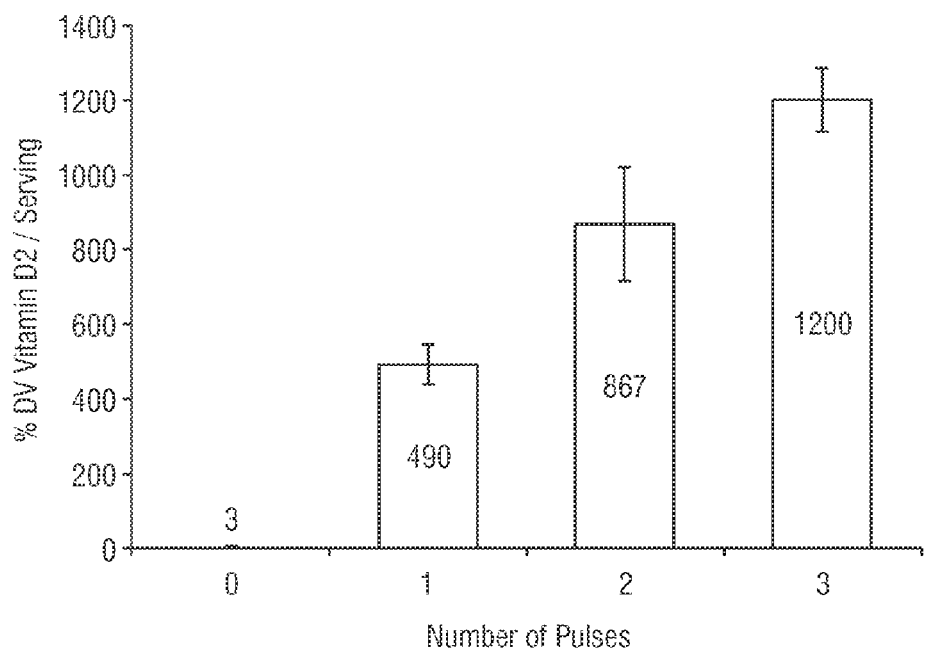
FIG. 9 is a graph depicting the percent DV Vitamin $D_2$ in one serving (84 g) of shiitake mushrooms (*Lentinula edodes*) after pulsed UV light exposure (B-type lamp). Error bars represent standard deviation of the two replications.

After Pulsed UV treatment fresh Shiitake mushrooms (FIG. 9) showed an increase in Vitamin $D_2$ content from an initial level of 3% DV/serving at 0 pulses to 490% DV/serving after one pulse. The Vitamin $D_2$ content after 3 pulses was 1200% DV/serving.

Figure 10:
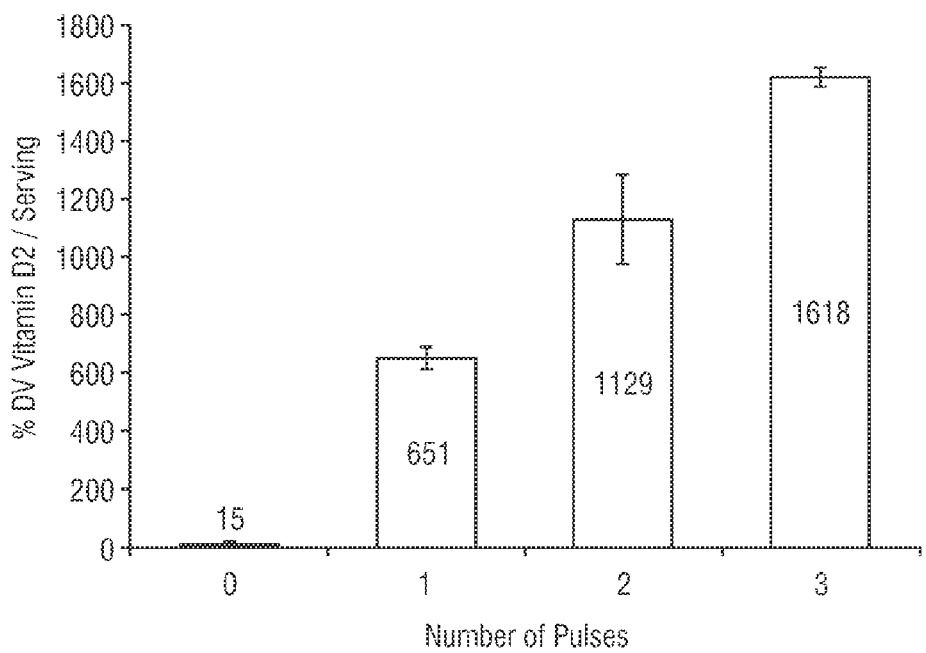
FIG. 10 is a graph showing the percent DV Vitamin $D_2$ in one serving (84 g) of oyster mushrooms (*Pleurotus ostreatus*) after pulsed UV light exposure (B-type lamp). Error bars represent standard deviation of the two replications.

Fresh Oyster mushrooms contained an initial level of Vitamin $D_2$ of 15% DV/serving at 0 pulses to a level of 1618% DV/serving after 3 pulses (FIG. 10).

The Oyster and Shiitake showed higher amounts of Vitamin $D_2$ content after Pulsed UV light exposure than the brown and white button mushrooms. This is most likely due to the thickness of the layer of mushrooms in the system. The brown and white button mushrooms were placed in polystyrene containers to simulate a package of sliced mushrooms being treated. The Oyster and Shiitake mushrooms were treated as whole mushrooms since their geometry did not permit for even distribution when packed together. The single layer of the Oyster and Shiitake mushrooms was similar to how these mushrooms would be treated if the Pulsed UV system were placed over a line where the mushrooms were being transported on a conveyor belt in a single layer. An additional study would be needed to directly compare the Vitamin $D_2$ content of the Agaricus mushrooms to the Oyster and Shiitake mushrooms.

This study demonstrates that after a very short exposure time of about 1 sec (system generates 3 pulses per second) the Vitamin $D_2$ content of these mushroom varieties can be increased from very little to upwards of 800% DV/serving. Previous studies using continuous UV light has been shown to take at least 5 minutes of exposure to obtain similar values (Feeney, 2006).

This study also showed that increasing the Vitamin $D_2$ contents of several mushroom products such as powders and substrates is possible. This material could be used as food ingredients or for animal feed to create value added products.

Figure 11:
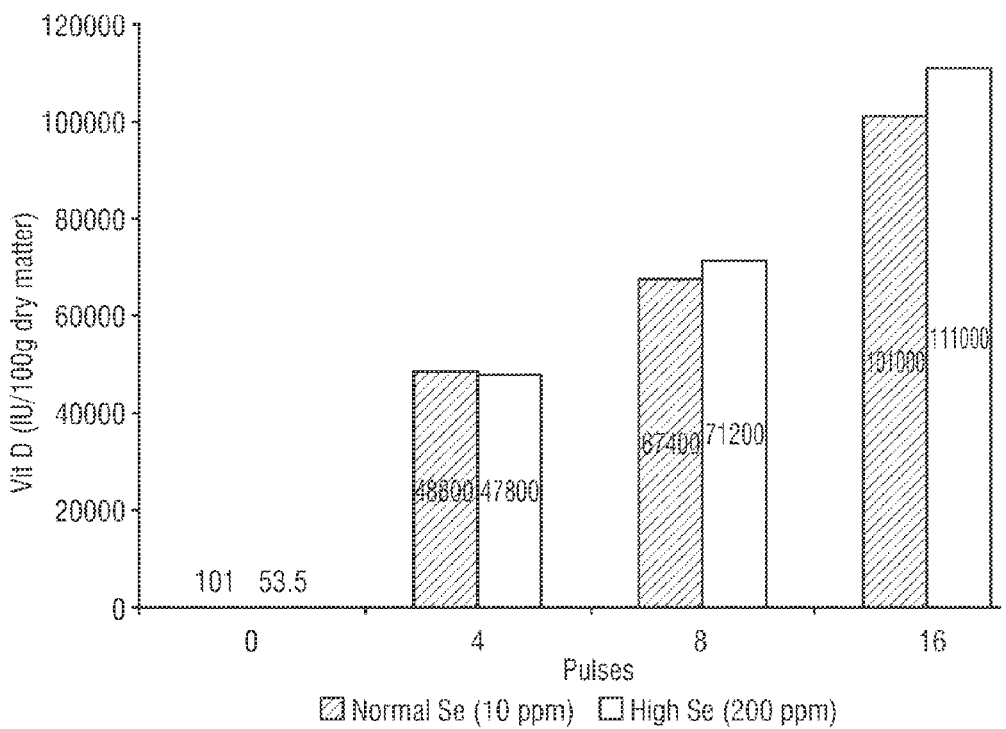
FIG. 11 is a graph showing the vitamin $D_2$ content of pulsed UV treated (B-type lamp) selenium enriched and normal air-dried *Agaricus bisporus* mushroom powder. Samples were treated at a distance of 3.2 cm.

FIG. 11 shows that the Vitamin $D_2$ content of selenium enriched (200 ppm) and control (10 ppm) mushroom powder (*Agaricus bisporus*) were increased in a similar manner from around 100 IU at 0 pulses to over 100,000 IU per 100 g with a treatment of 16 pulses.

Figure 12:
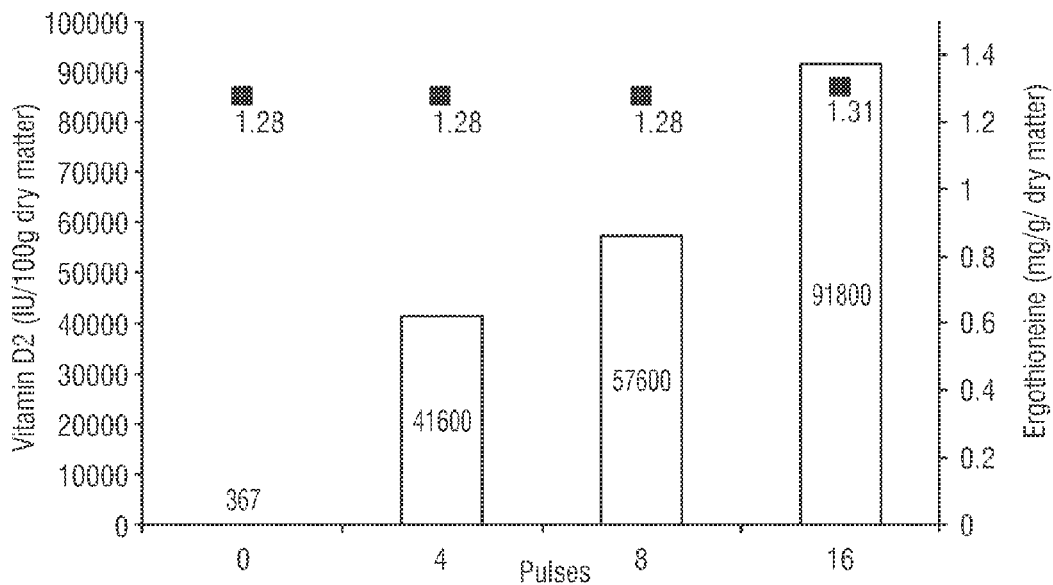
FIG. 12 is a graph showing the Vitamin $D_2$ and ergothioneine (black squares) contents of pulsed UV treated (B-type lamp) king oyster mushroom powder. Samples were treated at a distance of 3.2 cm.

The Vitamin $D_2$ content of air-dried King Oyster powder was increased from 367 IU at 0 pulses to 91800 IU per 100 g after 16 pulses. The ergothioneine content of the dried products remained constant around 1.3 mg/g for all treatments (FIG. 12) indicating that pulsed UV treatment had no effect on ergothioneine levels.

Figure 13:
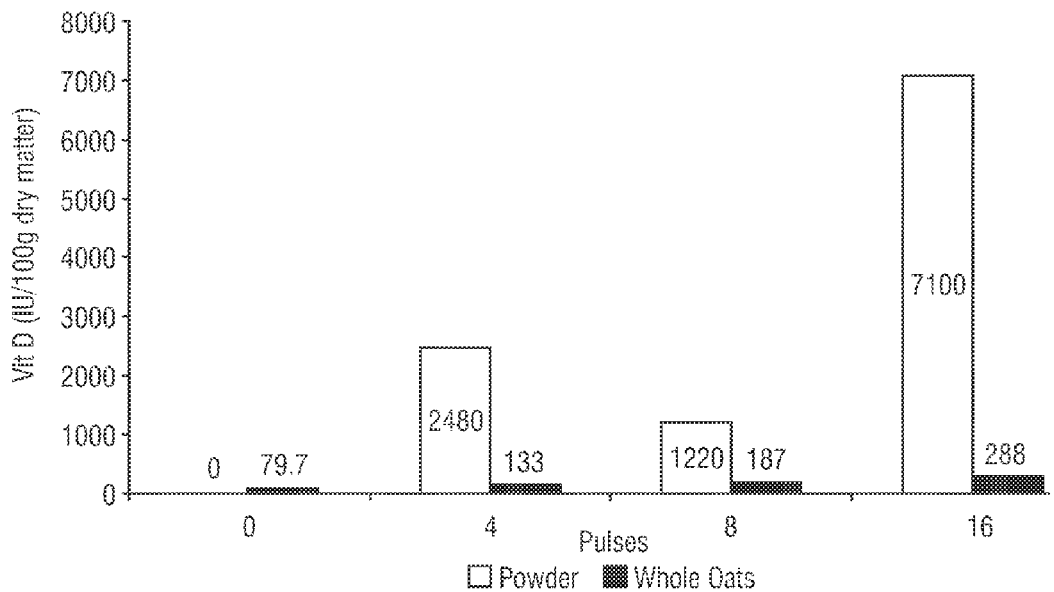
FIG. 13 is a graph depicting the Vitamin $D_2$ content of pulsed UV treated (B-type lamp) king oyster mycelium grown on oat substrate. Samples were treated at a distance of 3.2 cm in both whole oat and ground powder form.

Mushroom mycelial biomass grown on sterile organic oats showed similar increases in Vitamin $D_2$ with increasing exposure although levels were not as high as with pure fruiting body material. Vitamin $D_2$ dried King Oyster mycelial biomass increased significantly when ground from 0 to 7100 IU, however when exposed before grinding the level only rose to 288 IU (FIG. 13).

Figure 14:
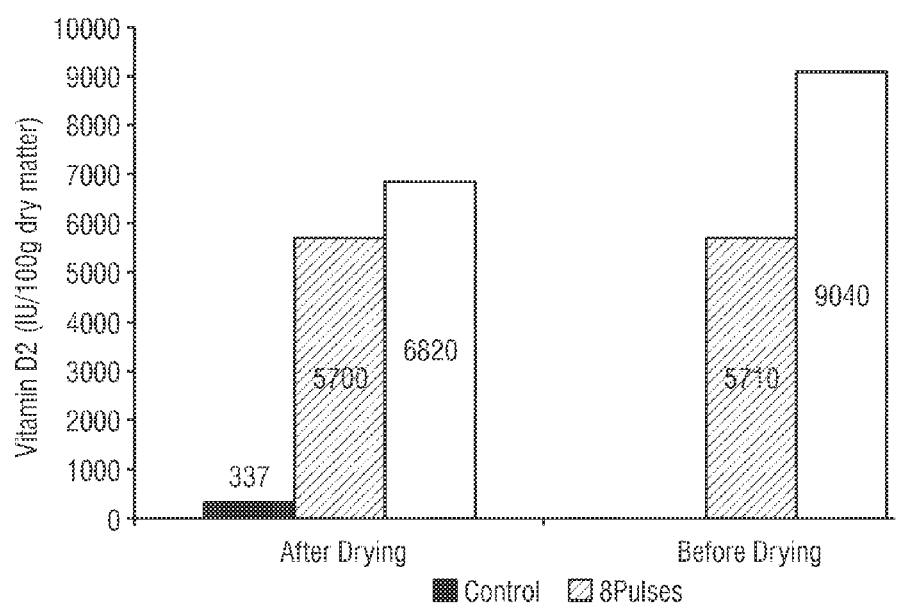
FIG. 14 is a graph showing the Vitamin $D_2$ content of pulsed UV treated (B-type lamp) spent king oyster substrate. Samples were treated wet and dry at a distance of 3.2 cm.
Figure 15:
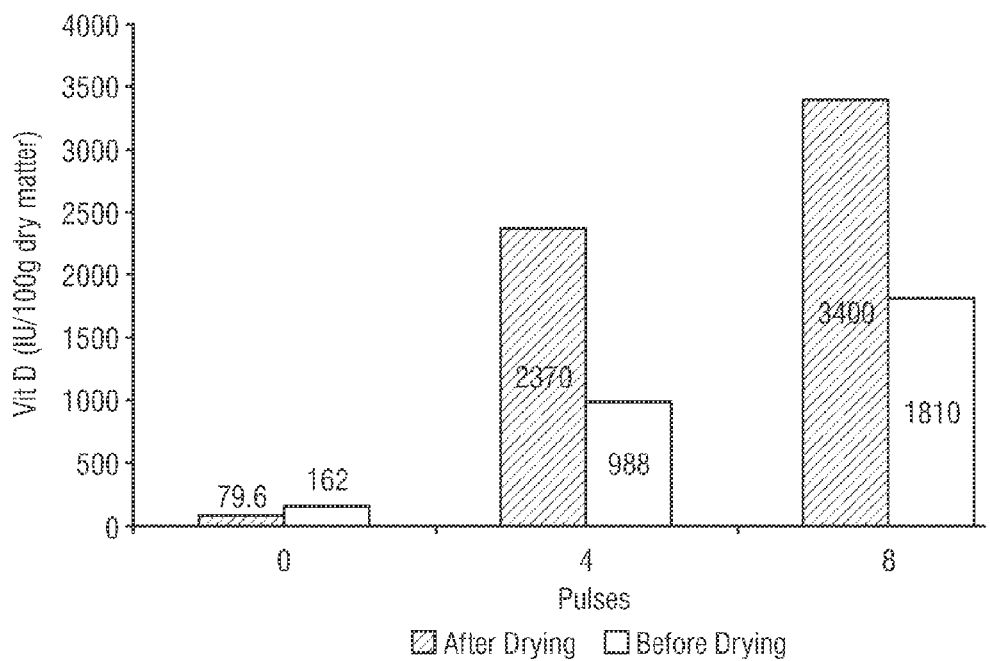
FIG. 15 is a graph depicting the Vitamin $D_2$ content of pulsed UV treated (B-type lamp) spent maitake substrate. Samples were treated at a distance of 3.2 cm before and after air-drying.

King Oyster spent substrates pressed of excess water and treated with pulsed UV light before and after air drying (FIG. 14) showed slightly higher Vitamin $D_2$ content when treated wet (9040 IU compared to 6820 IU at 16 pulses). The opposite effect was seen with Maitake spent substrate (FIG. 15). The undried substrate showed less conversion after 8 pulses (1810 IU compared to 3400 IU).

Pulsed UV technology has been shown to be a more practical method of UV irradiation of mushrooms for the mushroom industry than previous methods due to the shorter amount of time needed for exposure to achieve high amounts of Vitamin $D_2$. The UV-B bulb used in this study was found to be highly effective in converting ergosterol to Vitamin $D_2$ and would appear to more practical than UV-C bulbs for commercial use since there would be no generation of ozone that could compromise worker safety.

The ergothioneine content of mushrooms in both fresh and powder form did not appear to change much with pulsed UV treatment. These findings show that it is possible to produce mushrooms that contain high levels of selenium, Vitamin $D_2$ and ergothioneine.

EXAMPLE 2

Figure 16:
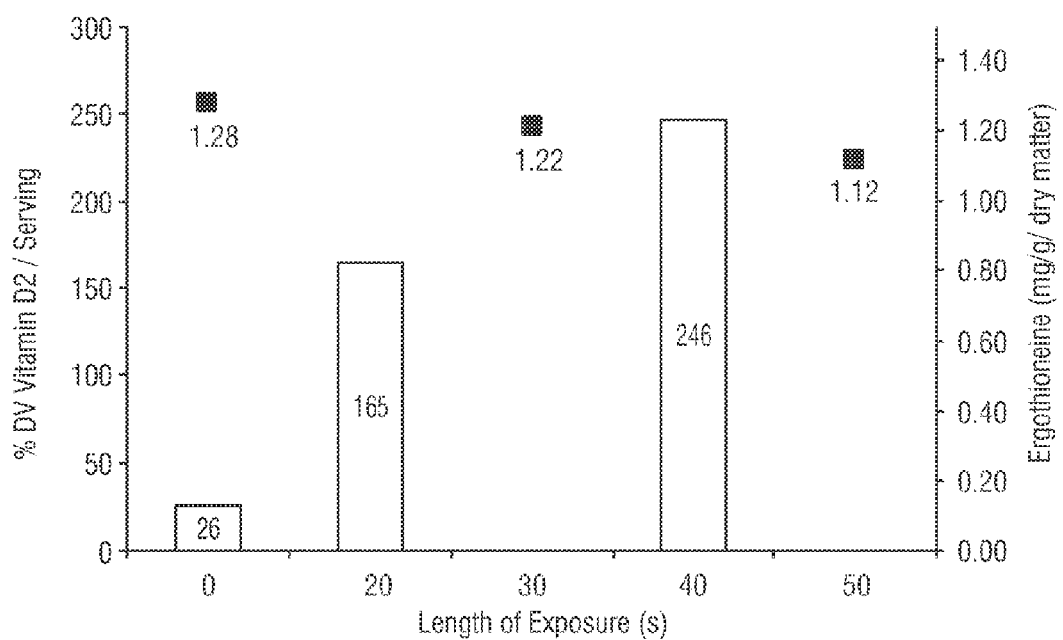
FIG. 16 is a graph showing the Vitamin $D_2$ and ergothioneine (black squares) contents of pulsed UV treated (C-type lamp) *Agaricus bisporus*. Samples were treated at a distance of 8 cm.

An experiment was conducted to determine if pulsed UV light treatment employed to enhance the Vitamin $D_2$ levels could have any negative effects on other nutritionally valuable components like the unique antioxidant L-ergothioneine. Sliced white button mushrooms were exposed to 0, 20, 30, 40 and 50 seconds of pulsed UV light as described above. The results (FIG. 16) demonstrate that Vitamin $D_2$ levels increased significantly with increasing time of exposure but L-ergothioneine levels were relatively unchanged. These data indicate that mushrooms can be enriched with Vitamin $D_2$ using pulsed UV light and high ergothioneine levels are retained.

While preferred embodiments of the present invention have been shown and described, it will be understood by those skilled in the art that various modifications can be made without varying from the scope of the invention.

What is claimed is:

1. A method of increasing the Vitamin D content of filamentous fungi, tissues, substrate, spent substrate or components thereof comprising:
irradiating said fungi with pulsed UV irradiation from a UV-B source wherein said pulse is approximately 1-10 J/cm$^2$ per pulse for a period of time of about 0.1 to about 60 seconds wherein approximately 1-50 pulses per second are provided, so that Vitamin D is increased without discoloration or deleterious effects on the appearance of the mushroom.

2. The method of claim 1 wherein said mushroom is exposed to a Xenon UV-B lamp.

3. The method of claim 1 wherein said UV irradiation is at an energy range of approximately 3-8 J/cm2.

4. The method of claim 1 wherein said UV irradiation is at an energy range of approximately 5-6 J/cm2.

5. The method of claim 1 wherein said pulses are at a range of approximately 1-30 pulses per second.

6. The method of claim 5 wherein said pulses are at a range of approximately 1-10 pulses per second.

7. The method of claim 6 wherein said pulses are at a range of 1-5 pulses per second.

8. The method of claim 1 wherein said treatment is for a time period of about 0.1 to about 10 seconds.

9. The method of claim 1 wherein said treat is at a distance of 3.2 cm from the window or 9 cm from the lamp.

10. The method of claim 1 wherein said mushroom is selected from the group consisting of *Agaricus bisporus*, *Lentinula edodes*, and *Pleurotus ostreatus*.

11. The method of claim 1 wherein said tissue is mycelium.

12. The method of claim 1 wherein said Vitamin D enriched component is mushroom substrate.

13. A method of increasing the Vitamin D content of filamentous fungi compromising:
obtaining a filamentous fungi, tissue, substrate, or component thereof to be enriched;
exposing said filamentous fungi, tissue, substrate, or component thereof to pulsed UV irradiation from a UV-B source wherein said pulse is approximately 1-10 J/cm$^2$ per pulse for a period of time of about 0.1 to about 60 seconds wherein approximately 1-50 pulses per second are provided, so that Vitamin D is increased without discoloration or deleterious effects on the appearance of the mushroom; and
removing said filamentous fungi tissue substrate or component from said exposure.

14. The method of claim 13 wherein said UV irradiation is at an energy range of approximately 3-8 J/cm2.

15. The method of claim 13 wherein said UV irradiation is at an energy range of approximately 5-6 J/cm2.

16. The method of claim 13 wherein said pulses are at a range of approximately 1-30 pulses per second.

17. The method of claim 16 wherein said pulses are at a range of approximately 1-10 pulses per second.

18. The method of claim 17 wherein said pulses are at a range of 1-5 pulses per second.

19. The method of claim 13 wherein said treatment is for a time period of about 0.1 to about 10 seconds.

20. The method of claim 13 wherein said treat is at a distance of 3.2 cm from the window or 9 cm from the lamp.

* * * * *